(12) United States Patent
Consiglio

(10) Patent No.: US 9,114,634 B2
(45) Date of Patent: Aug. 25, 2015

(54) RECORDER WITH PIEZO MOTOR USED TO DRIVE PLATEN FOR HIGH MAGNETIC ENVIRONMENTS

(75) Inventor: Ronald Paul Consiglio, Clermont, FL (US)

(73) Assignee: Koninklijke Philips N.V., Eindhoven (NL)

( * ) Notice: Subject to any disclaimer, the term of this patent is extended or adjusted under 35 U.S.C. 154(b) by 315 days.

(21) Appl. No.: 13/811,917

(22) PCT Filed: Jul. 18, 2011

(86) PCT No.: PCT/IB2011/053178
§ 371 (c)(1),
(2), (4) Date: Jan. 24, 2013

(87) PCT Pub. No.: WO2012/014119
PCT Pub. Date: Feb. 2, 2012

(65) Prior Publication Data
US 2013/0123608 A1 May 16, 2013

Related U.S. Application Data

(60) Provisional application No. 61/368,306, filed on Jul. 28, 2010.

(51) Int. Cl.
| | |
|---|---|
| *B41J 29/38* | (2006.01) |
| *B41J 11/00* | (2006.01) |
| *A61B 5/00* | (2006.01) |
| *G01R 33/28* | (2006.01) |
| *B41J 3/44* | (2006.01) |
| *A61B 5/055* | (2006.01) |

(52) U.S. Cl.
CPC .............. *B41J 3/445* (2013.01); *A61B 5/0002* (2013.01); *A61B 5/055* (2013.01); *B41J 29/38* (2013.01); *G01R 33/28* (2013.01); *B65H 2555/14* (2013.01); *B65H 2555/27* (2013.01)

(58) Field of Classification Search
CPC ...... B41J 3/455; B41J 3/445; B65H 2555/14; B65H 2555/28; B65H 2555/27
See application file for complete search history.

(56) References Cited

U.S. PATENT DOCUMENTS 4,483,346 A * 11/1984 Slavin ........................... 600/523
5,988,789 A * 11/1999 Nakahara ........................ 347/32
(Continued)

FOREIGN PATENT DOCUMENTS

| JP | 62077969 A | 4/1987 | |
|---|---|---|---|
| JP | 05155454 A * | 6/1993 | ............... B65H 5/00 |
| JP | 05185670 A | 7/1993 | |
| JP | 09208080 A * | 8/1997 | ............... B65H 5/06 |
| WO | 2007134146 A2 | 11/2007 | |

(Continued)

OTHER PUBLICATIONS

Maeda, H., et al.; A Cylindrical Ultrasonic Motor for NMR Sample Spinning in High Magnetic Field; 2009; IEEE Trans. on Intl. Ultrasonics Symposium; pp. 1070-1073.

*Primary Examiner* — Daniel J Colilla

(57) ABSTRACT

An apparatus and method generates a print out of physiological information from a patient (4) undergoing a magnetic resonance scan in a magnetic resonance system (8). The magnetic resonance system includes a main magnet that generates a static magnetic field ($B_0$) through an examination region (12). A recorder device (38) is located adjacent the patient within a five Gauss line and more particularly, in the examination region with the patient at full field. A piezoelectric motor (68) drives a pinion (72) which drives a roller platen (62) of a printer assembly (60). A primary controller board (70) generates electromechanical stepper motor drive signals (90) and a secondary controller board (74) converts the electromechanical stepper motor drive signals (90) to piezoelectric motor drive motor signals (100).

17 Claims, 4 Drawing Sheets

(56) References Cited

Figure 1:
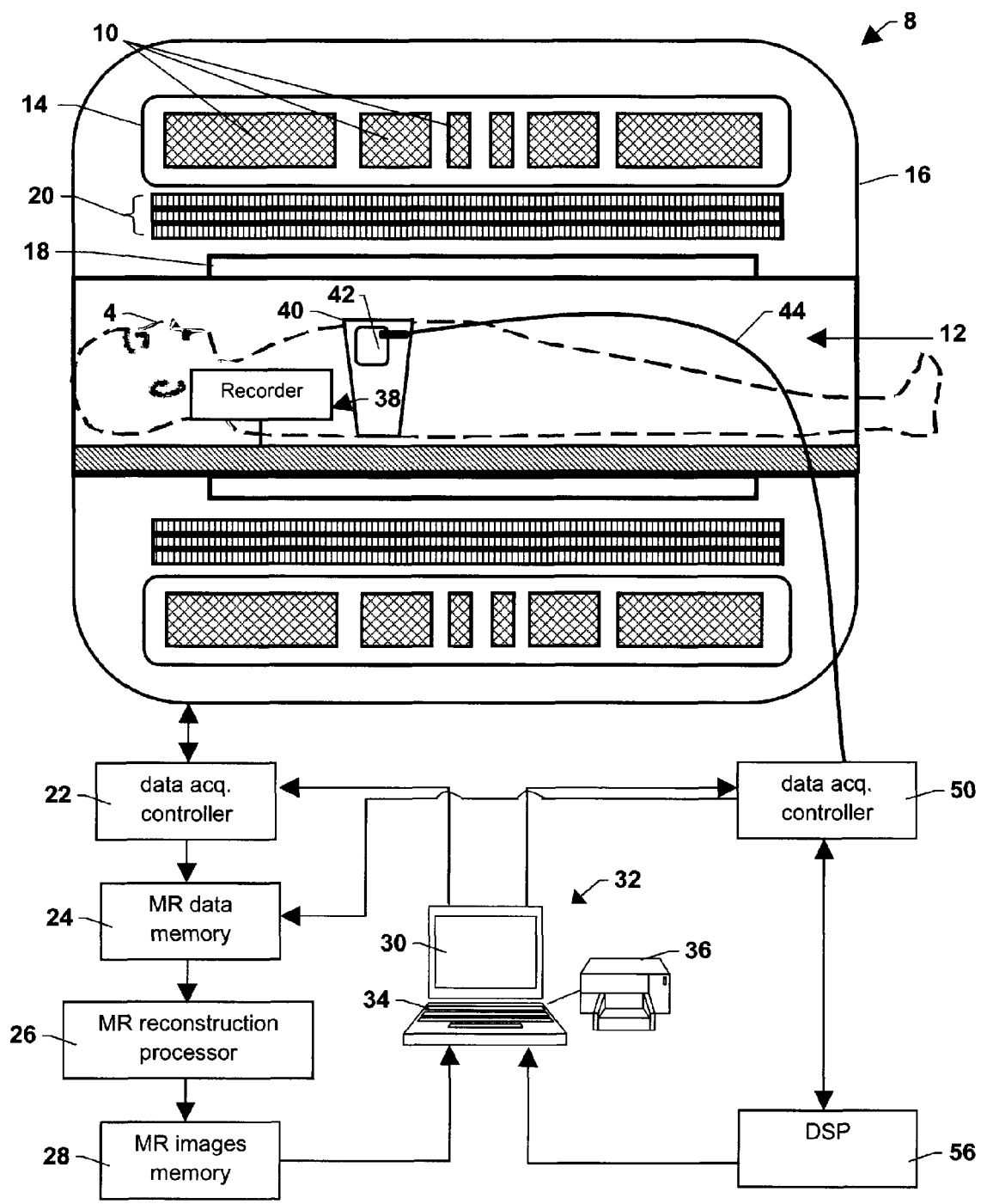

U.S. PATENT DOCUMENTS 6,274,965 B1    8/2001    Daum et al.
2010/0245518 A1*    9/2010    Matsumoto et al. .......... 347/104

FOREIGN PATENT DOCUMENTS

WO    2009107008 A2    9/2009
WO    2010020184 A1    2/2010

* cited by examiner

RECORDER WITH PIEZO MOTOR USED TO DRIVE PLATEN FOR HIGH MAGNETIC ENVIRONMENTS

CROSS REFERENCE TO RELATED APPLICATIONS

This application is a national filing of PCT application Serial No. PCT/IB2011/053178, filed Jul. 18, 2011, published as WO 2012/014119 A1 on Feb. 2, 2012, which claims the benefit of U.S. provisional application Ser. No. 61/368,306 filed Jul. 28, 2010, which is incorporated herein by reference.

The following relates to the medical arts, magnetic resonance arts, diagnostic imaging arts, and related arts. It finds application in magnetic resonance imaging, spectroscopy and other magnetic applications that produce a strong magnetic field, and the like.

Conventional magnetic resonance imaging (MRI) and spectroscopy (MRS) uses powerful magnetic fields to align dipoles in a subject or patient at an examination region. Often, the suites that house the MRI magnets are shielded to prevent the powerful magnetic and radio frequency (RF) fields from interfering with other devices and stray RF fields from interfering with the MR system. One potentially dangerous side effect of the powerful magnetic fields is the physical attraction it exerts on nearby ferromagnetic material. Ferrous objects or objects with ferrous components must be kept at a safe distance away from the magnet when it is at field, typically beyond the 5 gauss line. Even if the magnetic attraction is not powerful enough to physically displace the device as a whole, the magnetic field still exerts forces and torques that affect the operation of the device. Another adverse side effect is that the magnetic field can damage magnetically sensitive instruments and cause them to fail or malfluncion. Even at distances where physically displacing the object is not a large danger, the magnetic fields can still affect sensitive components. This may be a temporary failure and once removed from the field the device may operate normally. However, permanent damage can be caused, such as by de- or re-polarizing permanent magnets, deformation, and the like. The magnetic forces on moving electromagnetic or ferrous parts can cause extra loading of the device leading to premature failure.

A recorder, for example, contains a drive roller for a strip of paper that is often driven by either a DC motor or a magnetic stepper motor, neither of which operates effectively within the magnetic field of a magnetic resonance system. The recorder may simply fail to operate within the magnetic field. Alternatively, the magnetic motor may lose magnetization, get re-polarized, run slow or even run in reverse, especially if brought close to the main magnet of an MR system where magnetic field strength strength is high, such as within the five gauss line. It is sometimes advantageous to have the recorder record physiological data closely adjacent a patient undergoing an MR examination. For example, the recorder could be built into an ECG monitor, a blood pressure monitor, or the like. When the recorder is closely adjacent the patient undergoing the MR examination, the recorder, like the patient, is subject to substantially the full field.

The following provides a new and improved apparatus and methods which overcome the challenges discussed above and others.

In accordance with one aspect, a recorder device is provided for recording physiological data from a patient disposed in a high magnetic field. The recorder device includes a print head assembly which prints the physiological data from the patient disposed in the high field. A piezoelectric motor feeds paper through the printer assembly as the physiological data from the patient in the high magnetic field is printed.

In accordance with another aspect, a method of generating a printout of physiological data from a patient disposed in a high magnetic field is provided. The physiological data from the patient in the high magnetic field is monitored. A piezoelectric motor is controlled to feed paper past a print head which prints the monitored physiological data on the paper.

One advantage resides in driving a recorder in the presence of a strong magnetic field.

Another advantage resides in printing patient information in close proximity of an MR system.

Another advantage resides in recording physiological data in an MR environment without introducing problematic electrically conductive paths or loops from long connections.

Further advantages of the present invention will be appreciated to those of ordinary skill in the art upon reading and understand the following detailed description.

FIG. 1 diagrammatically shows a combined magnetic resonance data acquisition system.

Figure 2:
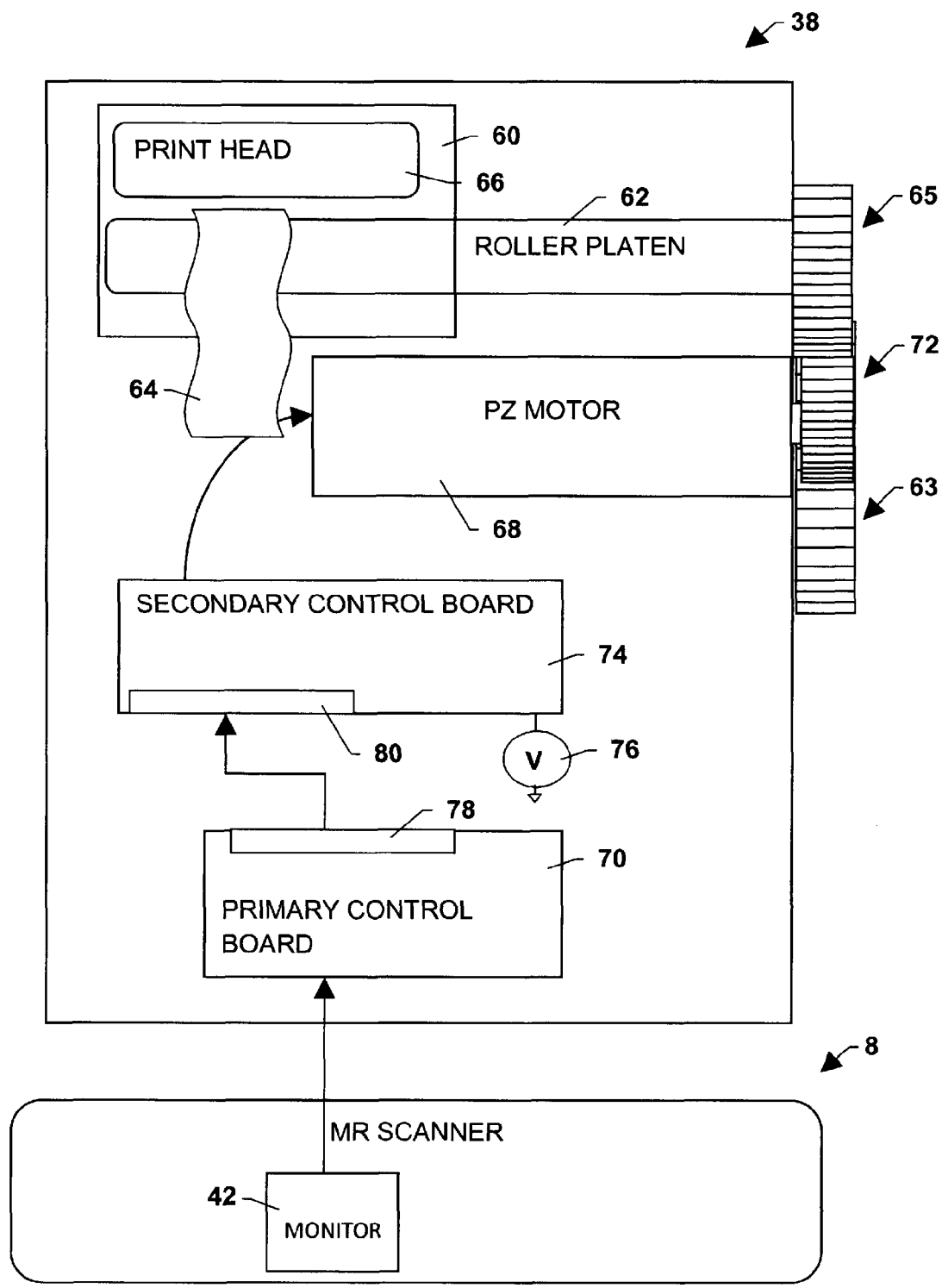

FIG. 2 diagrammatically shows a recorder device for use in the system of FIG. 1.

Figure 3:
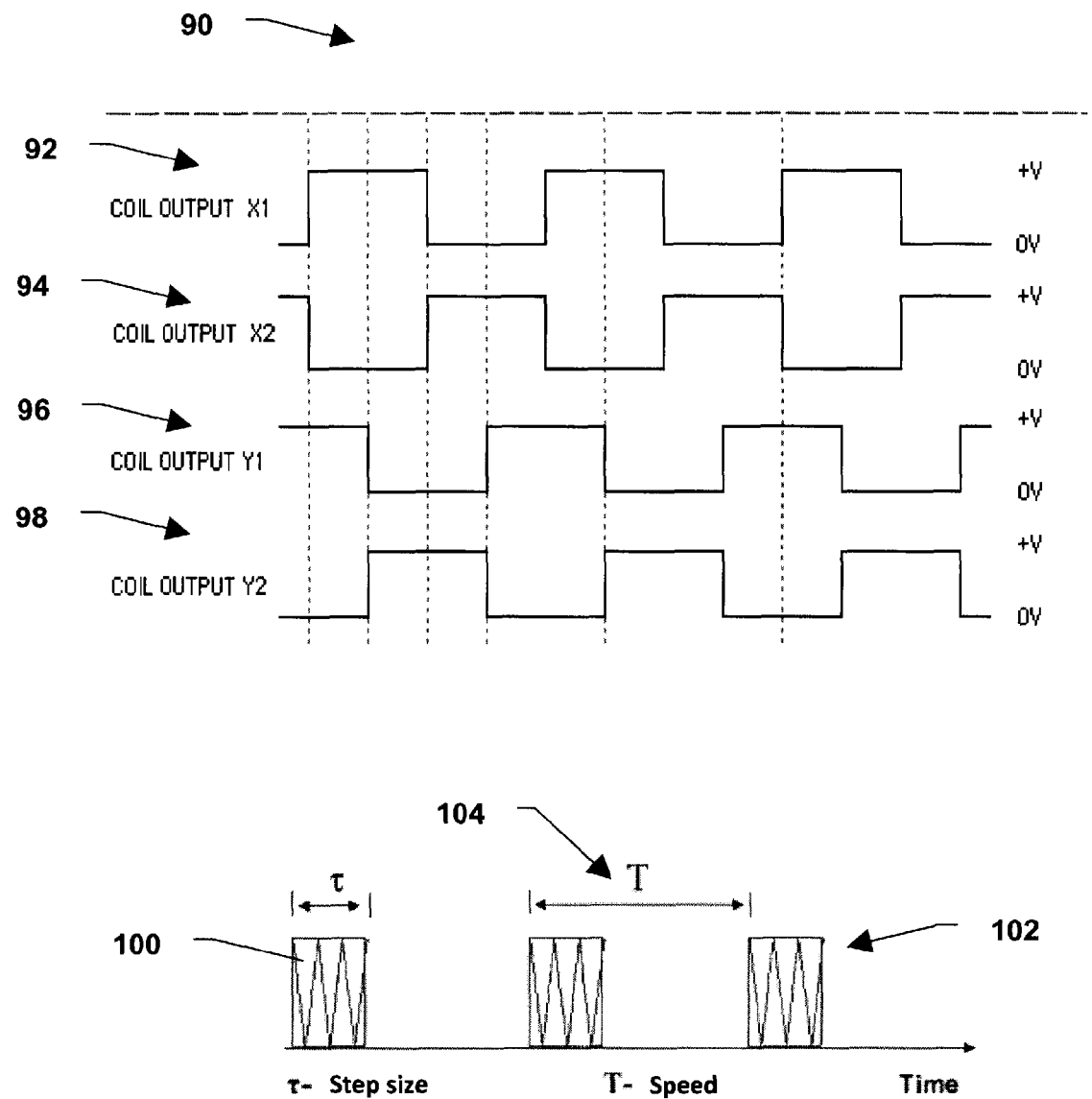

FIG. 3 diagrammatically shows power control signals adapted for driving the recorder device of FIG. 3.

Figure 4:
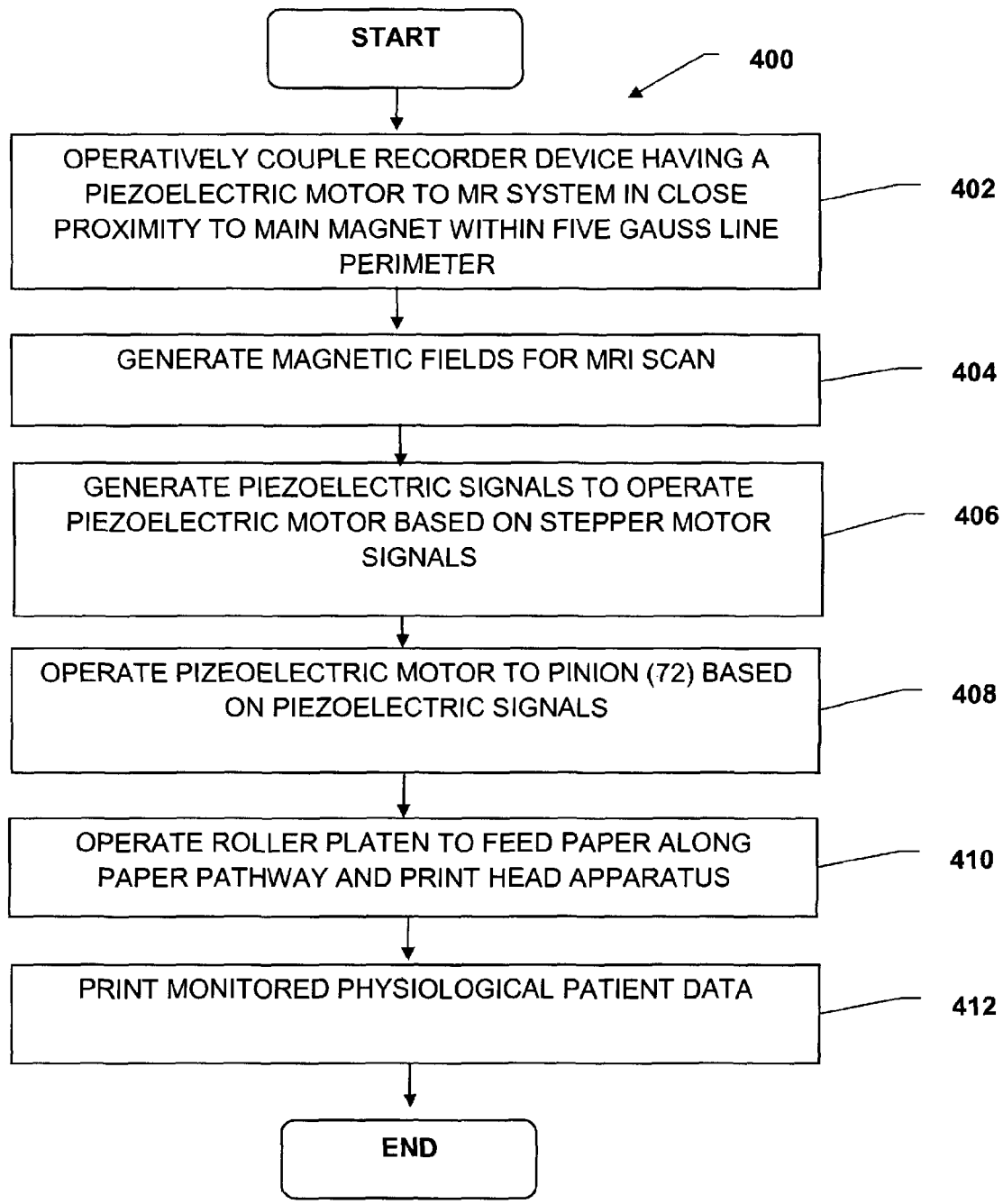

FIG. 4 illustrates a method for operating a recorder device to record patient information of a patient in an MR environment.

With reference to FIG. 1, a magnetic resonance (MR) system includes a MR scanner 8 having a main magnet 10 that generates a temporally static main ($B_0$) magnetic field in an examination region 12. In the illustrated embodiment, the main magnet 10 is a superconducting magnet disposed in a cryogenic vessel 14 employing helium or another cyrogenic fluid; alternatively a resistive main magnet can be used. In the illustrated embodiment, the magnet assembly 10, 14 is disposed in a generally cylindrical scanner housing 16 defining the examination region 12 in a bore, such as a cylindrical bore; alternatively, other geometries such as an open MR geometry can also be used. Magnetic resonance is excited and detected by one or more radio frequency coils, such as an illustrated whole-body quadrature body coil 18 or one or more local coils or coil arrays such as a head coil or chest coil. The excited magnetic resonance is spatially encoded, phase- and/or frequency-shifted, or otherwise manipulated by magnetic field gradients selectively generated by a set of magnetic field gradient coils 20.

The magnetic resonance scanner 8 is operated by a magnetic resonance data acquisition controller 22, suitably embodied by a dedicated digital processing device, a suitably programmed general purpose computer, or so forth, to generate, spatially encode, and read out magnetic resonance data, such as projections or k-space samples, that are stored in a magnetic resonance data memory 24. The acquired spatially encoded magnetic resonance data are reconstructed by a magnetic resonance reconstruction processor 26 to generate one or more images of a patient subject 4 disposed in the examination region 12. The reconstruction processor 26 employs a reconstruction algorithm comporting with the spatial encoding, such as a backprojection-based algorithm for reconstructing acquired projection data, or a Fourier transform-based algorithm for reconstructing k-space samples.

A computer interface system 32 also includes one or more user input devices such as an illustrated keyboard 34, or a mouse or other pointing-type input device, or so forth, which enables a radiologist, cardiologist, or other user to manipulate images and, in the illustrated embodiment, interface with the magnetic resonance scanner controller 22. The one or more reconstructed images are stored in a magnetic resonance images memory 28, and are suitably displayed on a display 30 of the computer interface system 32, or printed using a printer or other marking engine 36; alternatively, images may be transmitted via the Internet or a digital hospital network, or stored on a magnetic disk or other archival storage, or otherwise utilized.

With continuing reference to FIG. 1, the MR system 8 includes a physiological monitor device 42 that may include various sensors that are operatively connected to the patient 4. The diagnostic sensing device 42 may be be included in a respiratory sensor, an invasive or non-invasive blood pressure sensor, ECG, SP02, or any other medical device operative to sense different types of physiological patient data within the physiological examination region 12 of the MR system 8. In one embodiment the physiological monitor 42 includes a cuff or belt 40 that extends around a patient's limb or a torso, e.g. to sense changes in blood pressure. The physiological monitor can also include ECG electrodes, other cardiac monitors, and the like. The present disclosure is not limited to any particular medical device. The physiological monitor 42 senses stimuli proximate to or within the examination region 12. The physiological monitor includes or sends the physiological data to a recorder 38. Optionally, the monitor 42 transmits the physiological data wirelessly, via bluetooth, over a fiber optic or electric wire cable 44, or the like to a data acquisition controller 50. A digital signal processor 46 formats the physiological data for display on the monitor 30, for storage in a patient database, and the like.

Data sensed from the patient is sent to the recorder 38 located proximate to the main magnet 10 in the magnetic field. A recorder prints, e.g. on a paper strip chart, a record of the sensed physiological data. The recorder device 38 is located and operates at full field, e.g., 1.5 T, 3 T, etc. The cuff 40 may include electrodes or other sensing components constructed of materials having low magnetic susceptibility and/or include small-sized components (such as electrodes) of higher magnetic susceptibility, so as to not interfere with, or minimally interfere with, the magnetic resonance data acquisition.

With continuing reference to FIG. 1 and with further reference to FIG. 2, an illustrative embodiment of the recorder device 38 is suitable for operation within high magnetic fields generated by the main magnet the MR scanner 8, where permanent magnet motors are hindered. The recorder device 38 includes a printer assembly 60 having a print head 66 and a platten roller 62 that are operable to record information of a patient, such as on paper 64 fed along a paper pathway therebetween. In one embodiment, the print head 66 includes a thermal print head for printing to the paper 64. The recorder 38 includes a piezoelectric motor 68 that drives the platen roller 62 via a roller platen pinion 65 for feeding the paper 64 past the print head. The piezoelectric motor 68 is an electric motor based upon a piezoelectric effect, e.g. a change in shape of a piezoelectric material when an electric field is applied. The material produces mechanical, acoustic, or ultrasonic vibrations, for example, in order to produce a linear or rotary motion, depending on the type of piezoelectric motor. A rotary piezoelectric motor provides a rotary motion for turning a piezoelectric motor pinion 72. A linear piezoelectric motor uses a mechanical interface to convert the linear motion into rotary motion.

In one embodiment, a primary control board 70 generates electromagnetic stepper motor pulses for driving a conventional electromechanical stepper motor. The primary control board 70 includes or interfaces with a clock to generate the pulses at a selected frequency to advance the paper 64 at a selected speed. The primary circuit board includes an interface 78 that sends the pulses to a secondary control board 74.

The secondary control board 74 converts the received pulses to control signals suitable for driving the piezoelectric motor 68 in a manner that mimics the prior art electromechanical stepper motor to drive the paper at the same selected speed and based on the signals received by the primary control board 70. The piezoelectric motor control signals include pulses of a predetermined size, e.g., pulse width and amplitude, and frequency to operate the piezoelectric motor 68 at rotational speeds analogous to the electromagnetic stepper motor. For example, by supplying excitation frequency in pulses of a known time and repetition rate, the piezoelectric motor 68 is made to mimic the action of the electromagnetic stepper motor. An electromagnetic stepper motor, for example, operates in steps where a saw-toothed gear turns about 7.5 degrees in angle per step. A piezoelectric stepper motor steps in smaller step and uses about 27,000 piezoelectric excitation pulses to create 7.5 degrees of rotary motion, i.e. the resolution of a piezoelectric motor is about 1 arc-second per pulse. The translation of the electromechanical stepper motor pulses generated at the primary control board 70 to the higher frequency control pulses for the piezoelectric motor is performed by the secondary control board 74. The printer assembly further includes an idler wheel 63 configured to transport motion from the piezoelectric motor pinion 72 operated by the piezoelectric motor to the roller platen. Because the piezoelectric motor 68 operates at a higher voltage than an electromechanical stepper motor, a power source 76 is provided. The power source can be an external power source or internal to the secondary control board 74 for driving the piezoelectric motor 68.

With reference to FIG. 3, output signals 102 from the primary control board 70 and secondary control board 74 of FIG. 2 are illustrated. Electromechanical stepper motor signals 90 demonstrate the nature of a stepper motor action that is imitated by a piezoelectric motor in the present disclosure. A polyphase AC synchronous electromechanical motor is ideally driven by sinusoidal current. A full step waveform, in which a stepper pinion is rotated, is a gross approximation of a sinusoid. Various drive techniques have been developed to better approximate a sinusoidal drive waveform, such as half stepping and microstepping, which one of ordinary skill in the art can appreciate.

For example, electromechanical stepper motors typically have multiple "toothed" electromagnets arranged around a stepper motor pinion, e.g., four electromagnets arranged at opposite sides of the pinion. The electromagnets (not shown) are energized by the primary control board circuit 70 and driven according to the electromechanical stepper motor signals 90. To make the motor shaft turn, a first electromagnet along an axis is given power by the power control output signals 92, which makes the pinion's teeth magnetically attracted to the electromagnet's teeth. When the pinion's teeth are thus aligned to the first electromagnet, they are slightly offset from the next electromagnet, and thus, when the next set of electromagnets is turned on with power control output signal 94, the first is turned off, the gear rotates slightly to align with the next one, and from there the process is repeated with power control signals 96 and 98. Each of these slight rotations is called a "step," with an integer number of steps making a full rotation. In that way, the motor can be turned by a precise angle, which typically is about 7.5 degrees.

Piezoelectric motors are typically driven by dual orthogonal vibration modes with a phase difference of about 90°. The contact point between two surfaces vibrates in an elliptical path, producing a frictional force between the surfaces. Usually, one surface is fixed causing the other to move. For example, in many piezoelectric motors a piezoelectric crystal is excited by a piezoelectric excitation signal 100 at the resonant frequency or excitation frequency of a piezoelectric motor. The signal 100 is provided in pulses 102 of higher frequency piezoelectric signals of a known time τ and repetition rate 104 to imitate the characteristic actions of the electromagnetic stepper motor and to drive the pinion 72. Thus, the roller platen 82 of a recorder device is turned for printing patient information in an MR system. For example, about 27,000 excitation pulses are generated to create a 7.5 degree motion of a stepper motor.

One embodiment of methodology 400 for generating a print out of data corresponding to patient information obtained during a magnetic resonance imaging (MRI) scan with a magnetic resonance (MR) system having a main magnet and a recorder device is illustrated in FIG. 4. While the method 400 is illustrated and described below as a series of acts or events, it will be appreciated that the illustrated ordering of such acts or events are not to be interpreted in a limiting sense. For example, some acts may occur in different orders and/or concurrently with other acts or events apart from those illustrated and/or described herein. In addition, not all illustrated acts may be required to implement one or more aspects or embodiments of the description herein. Further, one or more of the acts depicted herein may be carried out in one or more separate acts and/or phases.

The method 400 initializes at start and at 402 the recorder device 38 is operatively associated with a patient located within a close proximity to the main magnet of the MR system. During an MR examination, the recorder device is typically located within the five gauss line perimeter of the MR system and typically at full field. Magnetic and RF fields are generated for the MRI scan at 404 in order to generate magnetic resonance patient data in a physiological region, for example.

At 406, the higher frequency piezoelectric signals are generated by the secondary control board 74 based on stepper motor signals from the primary control board 70 of the recorder device 38. The piezoelectric signals operate the piezoelectric motor 68 with similar mechanisms to rotate the stepper motor pinion 72 at 408. For example, the piezoelectric signals are generated by the secondary control board 74 converting the electromechanical stepper motor signals 90 from the primary control board to the piezoelectric signals 100. A number of the piezoelectric motor signals are generated to imitate the corresponding electromechanical stepper motor actions in the piezoelectric motor. The piezoelectric signals 100 have a number of the pulses 102 in accordance with the piezoelectric excitation frequency provided at predetermined times and predetermined rates based on the electromechanical stepper motor signals 90 to operate the piezoelectric motor in similar manner to the stepper motor.

The roller platen 62 is turned at step 410 via the pinion 65 coupled thereto and the paper 64 is fed along the paper pathway in response to the piezoelectric signals driving the piezoelectric motor 68. In a step 412, the print head responds to physiological data from the monitor 42 to print a representation of the monitored physiological patient data, such as an ECG chart, a blood pressure chart, symbols indicating the occurrence and termination of events, periodically read numerical data, or the like.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus describe the preferred embodiments, the invention is now claimed to be:

1. A recorder device for recording physiological data from a patient disposed in a high magnetic field, the recorder device comprising:
   a printer assembly which prints the physiological data from the patient disposed in the high magnetic field;
   a piezoelectric motor disposed in the high magnetic field configured to feed paper through the printer assembly as the physiological data from the patient in the high magnetic field is printed;
   a primary control board that is configured to generate electromechanical stepper motor drive signals based on clock signals;
   a secondary control board operatively connected to the primary control board and the piezoelectric motor to receive the stepper motor drive signals from the primary control board and generate piezoelectric motor drive signals that drive the piezoelectric motor.

2. The recorder device according to claim 1, the printer assembly includes a print head which prints the physiological data and a roller platen which feeds the paper past the print head, and
   the piezoelectric motor is operatively coupled to the printer assembly to rotate the roller platen and feed the paper past the print head.

3. The recorder device according to claim 1, wherein the electromechanical stepper motor drive signals are configured to feed the paper at a preselected speed and the secondary control board reconfigures the electromechanical stepper motor drive signals to piezoelectric drive signals that drive the piezoelectric motor to feed the paper at said preselected speed.

4. The recorder device according to claim 1, wherein the secondary control board includes a power source electrically coupled thereto which increases an amplitude of the piezoelectric motor signals.

5. The recorder device according to claim 1, wherein the secondary control board is configured to drive the piezoelectric motor directly without an external power source coupled thereto.

6. The recorder device according to claim 1, wherein about 27,000 pulses of the piezoelectric motor drive signal create 7.5 degrees of rotary motion.

7. The recorder device according to claim 1, further including:
   a monitor operatively connected to the printer assembly which displays the physiological data from the patient disposed in the high magnetic field.

8. The recorder device according to claim 1, wherein the printer assembly includes a thermal print head.

9. The recorder device according to claim 1, wherein the piezoelectric motor includes:
   a rotary piezoelectric motor configured to rotate a pinion, the pinion being mechanically coupled to a roller platen via a platen roller pinion.

10. An MRI system comprising:
    a main magnet which generates a static magnetic field in a patient examination region;

gradient coils which impose gradient magnetic fields on the static magnetic field;

radio frequency coils which apply radio frequency fields to induce and manipulate magnetic resonance;

a controller which controls the gradient and radio frequency coils and acquires resonance information from a patient located in the examination region; and the recorder device according to claim 1 disposed in or adjacent the examination region to print the physiological data from the patient in the examination region.

11. A method for generating a print out of physiological data from a patient disposed in a high magnetic field, comprising:

monitoring the physiological data from the patient in the high magnetic field;

controlling a piezoelectric motor located in the high magnetic field to feed paper past a print head including:

generating mechanical stepper motor drive signals based on clock signals;

generating piezoelectric motor drive signals which drive the piezoelectric motor from the mechanical stepper motor drive signals;

with the print head, printing the monitored physiological data on the paper.

12. The method according to claim 11, wherein generating the piezoelectric motor drive signals includes generating a number of pulses at a piezoelectric excitation frequency provided at predetermined times and predetermined rates based on the stepper motor drive signals.

13. The method according to claim 12, wherein about 27,000 pulses of the piezoelectric motor drive signals create 7.5 degrees of rotary motion.

14. The method according to claim 11, further including:

with the piezoelectric motor, rotating a stepper motor pinion that is mechanically coupled to a roller platen via a platen roller pinion that feeds the paper past the print head which prints the monitored physiological data.

15. The method according to claim 11, wherein the physiological data is monitored and printed during a MR scan of the patient.

16. A method for operating an MRI system comprising:

generating static magnetic fields through a patient;

imposing gradient magnetic fields on the static magnetic fields;

inducing radio frequency fields in the patient;

acquiring magnetic resonance information from the patient; and performing the method according to claim 11 to generate a print out of physiological data from the patient.

17. A recorder device for recording physiological data from a patient disposed in a high magnetic field, the recorder device comprising:

a printer assembly which prints the physiological data from the patient disposed in the high magnetic field;

a piezoelectric motor disposed in the high magnetic field configured to feed paper through the printer assembly as the physiological data from the patient in the high magnetic field is printed; and one or more circuit boards which generate stepper motor drive signals based on clock signals and generate piezoelectric drive signals from the stepper motor drive signals.

* * * * *